(12) United States Patent
Nufer

(10) Patent No.: US 11,786,200 B2
(45) Date of Patent: Oct. 17, 2023

(54) METHOD AND IMAGE RECORDING APPARATUS FOR OBTAINING IMAGE DATA FROM A PATIENT INVOLVING ADMINISTRATION OF A CONTRAST MEDIUM TO THE PATIENT

(71) Applicant: Siemens Healthcare GmbH, Erlangen (DE)

(72) Inventor: Stephan Nufer, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 671 days.

(21) Appl. No.: 16/395,834

(22) Filed: Apr. 26, 2019

(65) Prior Publication Data

US 2019/0328344 A1 Oct. 31, 2019

(30) Foreign Application Priority Data

Apr. 26, 2018 (DE) .......................... 102018206517.9

(51) Int. Cl.
*A61B 6/00* (2006.01)
*G16H 30/20* (2018.01)

(52) U.S. Cl.
CPC .............. *A61B 6/481* (2013.01); *A61B 6/463* (2013.01); *G16H 30/20* (2018.01)

(58) Field of Classification Search
CPC ....... A61B 6/463; A61B 6/481; A61B 6/5294; G16H 20/40; G16H 30/20
See application file for complete search history.

(56) References Cited

U.S. PATENT DOCUMENTS

2008/0119715 A1* 5/2008 Gonzalez Molezzi ...................... A61B 5/7285
600/407
2010/0113887 A1* 5/2010 Kalafut ................. A61M 5/007
600/300

(Continued)

FOREIGN PATENT DOCUMENTS

DE 102016207291 A1 11/2017

OTHER PUBLICATIONS

German action dated Dec. 3, 2018, Application No. 10 2018 206 517.9.

*Primary Examiner* — Boniface Ngathi
*Assistant Examiner* — Milton Truong
(74) *Attorney, Agent, or Firm* — Banner & Witcoff Ltd.

(57) ABSTRACT

In an image recording apparatus and an operation method therefor, image data of a patient are recorded with the use of a contrast medium administered to the patient. A computer of the image recording apparatus is provided with an image recording information item, describing the upcoming image recording carried out according to a multi-step sequence and with at least one patient information describing a property of the patient. The computer determines a contrast medium administration information item from these received information items, which designates at least one contrast medium quantity to be administered to the patient and a point in time in the sequence of the upcoming image recording. The contrast medium administration information item is displayed to a user of the image recording apparatus at the determined point in time on a display of the image recording apparatus.

18 Claims, 3 Drawing Sheets

(56) References Cited

U.S. PATENT DOCUMENTS

| | | | |
|---|---|---|---|
| 2012/0236995 A1* | 9/2012 | Eusemann | A61B 6/03 378/108 |
| 2013/0165755 A1* | 6/2013 | Thakur | A61B 5/686 600/301 |
| 2013/0165775 A1* | 6/2013 | Assmann | G16H 20/17 600/432 |
| 2015/0100572 A1* | 4/2015 | Kalafut | G16H 10/40 707/736 |
| 2017/0316562 A1 | 11/2017 | Haberland et al. | |

* cited by examiner

METHOD AND IMAGE RECORDING APPARATUS FOR OBTAINING IMAGE DATA FROM A PATIENT INVOLVING ADMINISTRATION OF A CONTRAST MEDIUM TO THE PATIENT

BACKGROUND OF THE INVENTION

Field of the Invention

The invention concerns a method for operating an image recording apparatus, which serves for recording image data of a patient. The invention also concerns an image recording apparatus and a non-transitory electronically readable storage medium that implement such a method.

Description of the Prior Art

In the examination of patients with the use of a medical image recording apparatus, it is often necessary, for example in the case of magnetic resonance tomography and computed tomography for imaging, to administer a contrast medium to the patient. With the contrast medium, particular anatomical structures of the patient, such as lesions of vessels or similar can be represented better, which enables an improved differential diagnosis. Before contrast media can be administered, it must first be ascertained by a physician whether the patient to be examined can tolerate the contrast medium intended for the corresponding imaging, and whether the patient has sufficient renal function to be able to eliminate the contrast medium again after the examination. Subsequently, a correct dosage of the contrast medium matched to the patient must be determined by the physician. This must be calculated anew for each contrast medium to be used and for each patient. Once the correct amount of the correct contrast medium has been determined for the patient, the contrast medium must then be administered at the correct point in time during the examination.

This procedure has the disadvantage that error can occur when calculating the dosage or when calculating a contrast medium quantity, and when taking account of the properties of the patient required for a contrast medium administration and equally when administering the contrast medium and the subsequent documentation, errors can occur. This procedure is also inefficient if the examination has to be interrupted for the calculation of the contrast medium quantity or the evaluation of patient data, so the duration of the examination is thereby prolonged.

SUMMARY OF THE INVENTION

An object of the present invention is to provide an improved method for operating an image recording apparatus that enables a more efficient operating procedure and reduces error sources in the preparation of a contrast medium administration.

This object is achieved by a method of the type initially described but wherein, in accordance with the invention, a computer or computer system of the image recording apparatus determines contrast medium administration information showing at least one contrast medium quantity to be administered to the patient and a point in time in the sequence of the future image recording, from image recording information item describing a future image recording to be carried out according to a multi-step sequence, and from patient information item describing a property of the patient. The contrast medium administration information item is displayed to a user of the image recording apparatus at the determined point in time on a display of the image recording apparatus.

Thus, with the computer or computer system of the image recording apparatus, dependent upon an image recording to be carried out and from at least one property of the patient, a contrast medium quantity to be administered to the patient for the image recording to be performed is determined, and is provided as part of the contrast medium administration information item. Furthermore, with the computer or computer system of the image recording apparatus, a point in time in the sequence of the image recording to be carried out in future is also determined, this point in time also being a part of the contrast medium administration information item. At the determined point in time, that is, during the process of the image recording, the contrast medium administration information is displayed to the user of the image recording apparatus on a the display, for example, a screen of the image recording apparatus, which means that the display is controlled accordingly at this point in time. In an embodiment, as part of the contrast medium administration information, at least one contrast medium to be administered can also be selected from a group of multiple contrast media that are available at the image recording apparatus.

The patient information item used for determining the contrast medium administration information describes at least one property of the patient that is relevant for the contrast medium administration (or, if provided, the contrast medium selection), which has an influence on the contrast medium administration in general and/or on the contrast medium quantity to be administered. The image recording information also taken into account in the determination of the contrast medium administration information item describes the multi-step sequence of the image recording to be carried out. The individual steps of the sequence are steps to be carried out chronologically sequentially by the image recording apparatus. The steps can individually be, for example, an initialization, a calibration, a patient positioning, a recording of image data and/or an ending of the image recording. In the determination of the contrast medium administration information item, both for the determination of the contrast medium quantity and for the determination of the point in time of the display of the contrast medium administration information item in the sequence of the image recording, the manner and/or the duration of the image recording, the sequence of the steps to be performed, the orientation in the recording of image data, and/or an orientation of the patient or the like can be taken into account.

A contrast medium administration information item is thus advantageously displayed to the user of the image recording apparatus at a most suitable possible point in time. At the determined point in time, the user therefore receives the possibility through the image recording apparatus of viewing the contrast medium administration information item relevant to a contrast medium administration displayed on the display screen. This avoids interruption of the examination and/or the image recording for the calculation of the contrast medium quantity by the user, and/or for a user search for the information relevant for the contrast medium administration regarding the image recording and/or the properties of the patient from different sources and/or different media. In addition, error sources in the preparation of the contrast medium administration can be avoided and the most efficient possible method sequence of the examination or the image recording can be enabled.

In an embodiment of the invention, the contrast medium administration information item is determined dependent upon a contrast medium information item, with the contrast medium information item being called from a database of the image recording apparatus or from a database connected to the image recording apparatus. The contrast medium information item describes the availability of one or more contrast media for the future (upcoming) image recording and one or more properties of the at least one available contrast medium, dependent upon the image recording information item. The contrast medium information item can thereby be called from the database by the computer or computer system of the image recording apparatus before the determination of the contrast medium administration information item. In the case of a database connected to the image recording apparatus, for this purpose a communication connection can exist between the computer or computer system of the image recording apparatus and the database, by which a request for the transfer of the contrast medium information item and the contrast medium information item can be transmitted. The contrast medium information item describes the availability of one or more contrast media for the future image recording. The availability can identify, for example, which contrast medium is present in the facility in which the image recording apparatus is operated. The image recording information item can advantageously be taken into account, so that from a set of available contrast media, only those contrast media that the contrast medium administration information item indicates are suitable for the future image recording can be taken into account. The contrast medium administration information item thus can designate, for each of the different contrast media that are available and that are suitable for the image recording, a contrast medium quantity determined dependent upon the patient information item. In the determination of this contrast medium quantity, one or more properties of the respective available contrast media can also be taken into account, dependent upon the image recording information item. Such a property may be a concentration of the contrast medium, which specifies a component-to-liquid ratio of a component of the contrast medium that is effective for an image recording, which is dissolved or suspended in a liquid. A dosage needed for the image recording, for example, volume per patient weight or substance quantity per patient weight, for a respective contrast medium and/or for an effective component of a respective contrast medium, can also be specified as a property.

The point in time can also be determined dependent upon the contrast medium information item, so that, if relevant, for different available contrast media, different respective point in times can also be determined dependent upon the image recording information item and/or the properties of the at least one available contrast medium. It is possible for one or more properties of the at least one available contrast medium, dependent upon the image recording information item, to also form part of the contrast medium administration information item. This enables the user of the image recording apparatus, at the determined point in time during the display of the contrast medium administration information item, to also take account of the one or more properties of the at least one available contrast medium.

The contrast medium information item thus represents a store of knowledge that is configured and/or configurable specifically to the image recording apparatus and/or to the medical device in which the image recording apparatus is operated, and which can be employed in a useful way. The contrast medium information item can be updated, such as when a user creates a special image recording protocol with special contrast medium requirements, or the like. An operating specificity of the image recording apparatus can also be provided, for example, the effect of particular properties and/or characteristics of the image recording apparatus on the usefulness, and the physical effects of, a particular contrast medium in the recording of image data, according to the image recording information item described by the contrast medium information item.

In accordance with the present invention, the patient information item and the image recording information item ultimately describe the physical conditions in the future image recording, and are linked to the physical properties of the contrast medium in order to enable a technically meaningful selection of the contrast medium administration information item, while also taking account of further patient properties. The contrast medium information item preferably provides further physical fundamental information in order, in an overview of technical details, to give a recommendation for the technical imaging process which is then actually carried out. Moreover, the contrast medium information item can lead to a suitable modification of the control of components of the image recording apparatus and/or additional devices.

In an embodiment of the invention, a user entry following a user entry of a confirmation information item into the computer or computer system, transfer of the contrast medium administration information item is made to an additional device connected to the image recording apparatus, which will be used in the future image recording. The confirmation information can be generated by the user via a user interface of the image recording apparatus. The entry of the confirmation information item by the user takes place following the display of the contrast medium administration information item on the display of the image recording apparatus. In this way, the user can take account of the contrast medium administration information item and subsequently initiate, through the generation of the confirmation information item, transfer of the contrast medium administration information item to the additional device. The additional device can be, for example, a contrast medium pump for administering the contrast medium to the patient that, after the transfer of the contrast medium administration information item, is thereby prepared or set for delivery of the contrast medium quantity described in the contrast medium information item. It is also possible that the additional device is an additional device that is used for the imaging and is arranged on the patient, such as a sensor or the like. Through the transfer of the contrast medium administration information item to the additional device, a setting and/or a function of the additional device can be undertaken while taking account of the contrast medium administration information item, so that the additional device can be adapted for the future image recording, for example, adapted to the contrast medium quantity.

In another embodiment of the invention, the displayed contrast medium administration information item is changeable by entry of a user input into the computer or computer system, after this change of the contrast medium administration information item, the changed contrast medium administration information item is transferred to the additional device. This allows a user of the imaging device to change the contrast medium administration information item displayed to him or her before the transfer to the additional device. The user can thereby change the contrast medium quantity that was automatically determined for a contrast medium. It is also possible for the user to select one of a number of available contrast media in the case where the contrast medium administration information item designates multiple contrast media. It is naturally also possible for the user to change the contrast medium administration information such that the contrast medium quantity to be administered is zero, and therefore no contrast medium administration should be carried out. If a change in the contrast medium administration information has been undertaken by the user, then subsequently the changed contrast medium administration information is transferred to the additional device, so that the changes undertaken then can be taken into account by the additional device.

In a preferred embodiment of the invention, the contrast medium administration information item is stored together with image data recorded during the image recording, as common storage data, in particular as storage data in the DICOM format. The contrast medium administration information item determined thus can be added to the image data as metadata, for example. In this way, a reliable documentation of the examination is simplified. The storage can take place during and/or following the execution of the future image recording, in particular during and/or following a recording of image data carried out during the contrast medium administration. Changes to the contrast medium administration information item undertaken by a user and/or a selection of a contrast medium made by the user can thereby also be stored.

In another embodiment of the invention, the image recording information item and/or the patient information item is called from a database of the image recording apparatus and/or from a radiology information system connected to the image recording apparatus. The radiology information system (RIS), which can form part of a hospital information system (HIS), can also include a database connected to the image recording apparatus in which an also-used contrast medium information item is stored. The use of a database or of a radiology information system, from which the image recording information item and/or the patient information item can be called, is advantageous to the efficiency of the inventive method, since interruptions or pauses during the image recording in which the corresponding data or information items are gathered by the user are avoided. Instead, the patient information items, which are usually gathered and/or read-in anyway during the registration, are also further used.

In another embodiment of the invention, the image recording information can include a scan protocol, or a sequence of a number of scan protocols, to be carried out by the image recording apparatus, each designating one or more control commands for operating the image recording apparatus (i.e., the scanner thereof). The point in time determined as part of the contrast medium administration information can conform to the scan protocol or the sequence of scan protocols so that point in time for the contrast medium administration during the image recording can be determined. The most suitable point in time can occur, for example, directly before the execution of a scan protocol that requires the use of a contrast medium or that achieves better results using a contrast medium. Thereby, the point in time can be selected by evaluating the control commands of the one or more scan protocols in the context of a pre-scan initialization and/or calibration of the image recording apparatus. The contrast medium information item can be displayed before the execution of the scan protocol, or before the execution of the part of a scan protocol that is actually dependent upon the contrast medium or can achieve advantageous results with use of the contrast medium. Erroneously administering the contrast medium too early or too late can thus be counteracted. In addition, especially in scan protocols with a number of contrast medium administrations and/or with a number of scan protocols of which only some involve contrast medium administration, no confusion occurs.

In another embodiment, the patient information item includes the weight of the patient and/or a laboratory value of the patient, in particular a creatinine value of the patient and/or a contrast medium intolerance information item of the patient. Naturally, the patient information can also include further data of the patient that are relevant for the administration of the contrast medium, such as at least one of the available contrast media, and data suitable for the execution of the examination, such as the name of the patient. The determination of the contrast medium quantity then takes place with the weight of the patient being taken into account so that, for the patient to be examined, and for one or more available contrast media, the suitable substance quantity or the suitable volume of the contrast medium is individually calculated. Furthermore, as noted the patient information can include at least one laboratory value that is relevant to the tolerance of at least one contrast medium. This can be, for example, a creatinine value of the patient, which provides information as to whether the patient has sufficient renal function for a contrast medium administration. The patient information can also include a contrast medium intolerance information of the patient, which indicates whether the patient to be examined has an intolerance to one or more contrast media, which was ascertained at an earlier point in time. In the determination of the contrast medium quantity dependent upon the patient information item, the aforementioned components of the patient information item can be taken into account such that the contrast medium quantity is adapted to the weight of the patient, for example. Furthermore, in the determination of the contrast medium quantity, the at least one laboratory value of the patient can also be taken into account. If a number of contrast media are available, then, in the determination of the contrast medium administration information item, contrast media for which a contrast medium intolerance of the patient is available, can be excluded.

In a preferred embodiment of the invention, at least one part of the patient information item relevant for a contrast medium administration is displayed simultaneously with the contrast medium administration information item at the determined point in time on the display screen of the image recording apparatus. The relevant part of the patient information item can be, in particular, the part of the patient information item that was taken into account for the determination of the contrast medium administration information item. The relevant part of the patient information item can be, for example, the weight of the patient and/or at least one laboratory value of the patient, in particular a creatinine value of the patient and/or a contrast medium intolerance information item of the patient. By the simultaneous display of at least the relevant part of the patient information item, in addition to the contrast medium administration information item, the user of the image recording apparatus is informed of at least the relevant part of the patient information item, and so can take account thereof for the further process of the examination or the image recording. The determination of the contrast medium administration information item is also plausibility-checked for the user.

The present invention also encompasses an image recording apparatus having a data acquisition scanner operated by a control computer (which may be composed of one or more computers or one or more processors). The control computer operates the imaging apparatus, or the scanner thereof, in order to implement any or all embodiments of the method according to the invention, as described above. The image recording apparatus may also include an additional device, as described above, which is involved in the acquisition of image data, or the administration of contrast agent, during the course of an image acquisition sequence in which contrast administration occurs.

The present invention also encompasses a non-transitory, computer-readable data storage medium encoded with programming instructions that, when the storage medium is loaded into a control computer of an image recording apparatus as described above, cause the control computer to operate the image recording apparatus so as to implement any or all embodiments of the method according to the invention, as described above.

DESCRIPTION OF THE PREFERRED EMBODIMENTS

Figure 1:
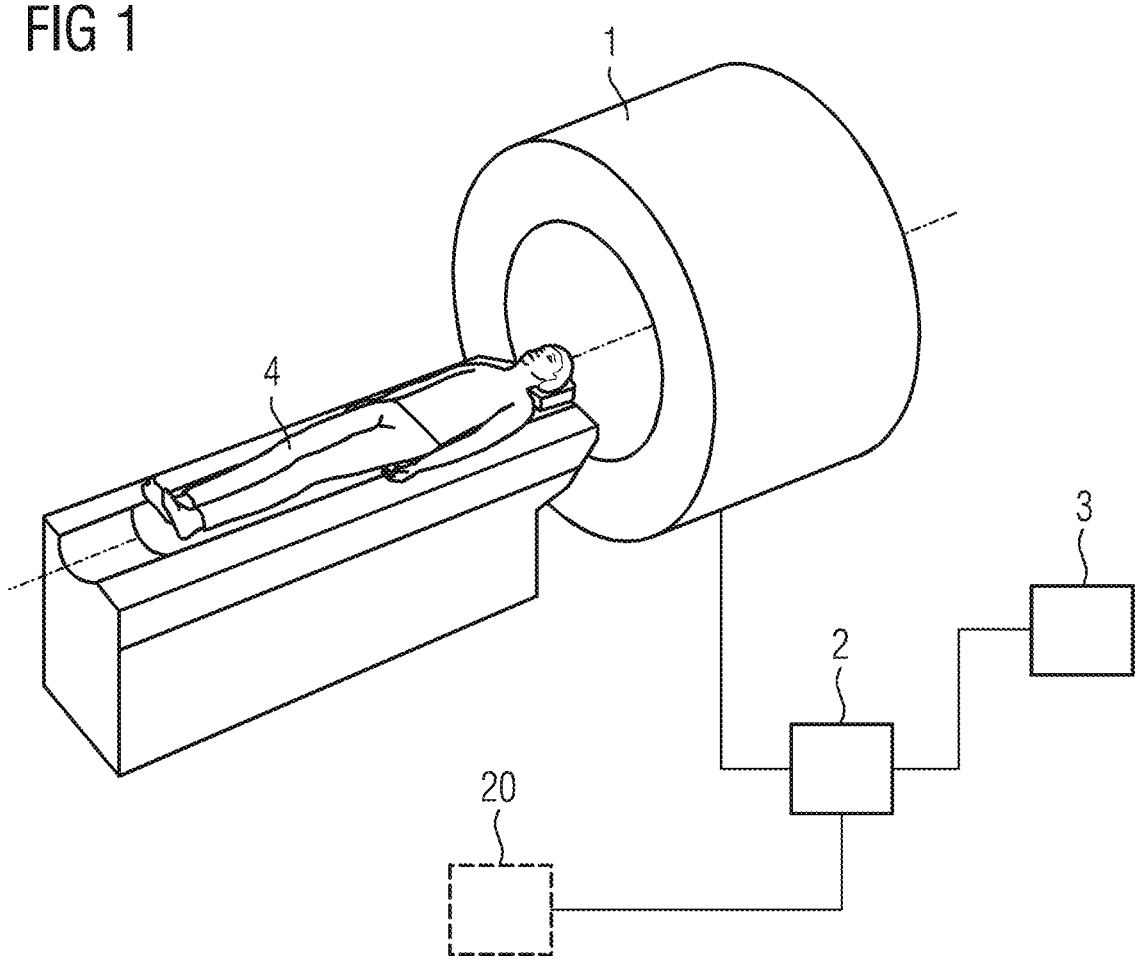
FIG. 1 a schematically illustrates an image recording apparatus according to the invention.

FIG. 1 schematically illustrates an image recording apparatus according to the invention. The image recording scanner 1 in the example shown is configured as a magnetic resonance imaging apparatus. It is also possible for the image recording apparatus to be an apparatus using a different imaging modality that uses a contrast medium during the imaging, for example, X-ray recording apparatuses or the like. The image recording apparatus further has a control computer 2 (which may be one or more computers or processors) and a display 3. The control computer 2 is configured to implement the method according to the invention.

In the inventive method, the control computer 2 uses an image recording information item, which describes a future (upcoming) image recording according to a sequence composed of multiple steps carried out by the image recording scanner 1, and a patient information item, describes at least one property of a patient 4, to determine a contrast medium administration information item. The contrast medium administration information item includes at least one contrast medium quantity to be administered to the patient 4 during the future image recording, and a point in time in the sequence of the future image recording carried out by the image recording apparatus 1. The contrast medium administration information item is displayed to a user of the image recording apparatus at the determined point in time on the display 3, which can be a display screen.

Figure 2:
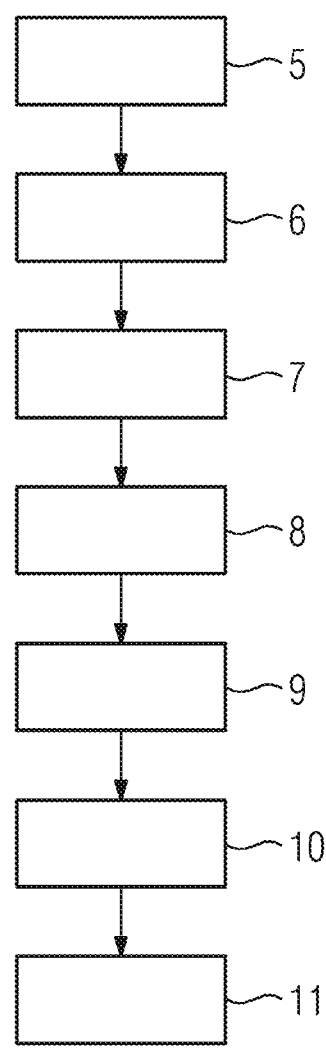
FIG. 2 is a flowchart of an exemplary embodiment of the method according to the invention.

FIG. 2 is a flowchart of the basic steps of the method according to the invention. The inventive method begins at step 5. The start of the method can take place, for example, at the point in time at which it is ascertained which patient 4 is to be examined in the image recording apparatus by which image recording. The start of the inventive method can thus take place as soon as the patient information and the image recording information are available. For example, the start of the method can take place while or after the patient 4 is being or has been positioned in the image recording apparatus.

In step 6, the determination of the contrast medium administration information takes place dependent upon the image recording information and the patient information. For this purpose, the patient information and the image recording information can be called from a database of the image recording apparatus. It is also possible for the patient information item and the image recording information item to be called by the control computer 2 from an external database connected to the control computer 2. The external database can be, for example, a radiology information system.

On the basis of the patient information item describing at least one property of the patient 4, and the image recording information describing the future executed image recording according to a sequence composed of multiple steps, the contrast medium administration information item is determined by the control computer 2. The contrast medium administration information item designates at least one contrast medium quantity to be administered to the patient as well as a point in time for the contrast agent administration in the sequence of the future image recording. It can also designate at least one contrast medium selected as an administration proposal from a quantity of available contrast media. The contrast medium information item can be determined additionally dependent upon a contrast medium administration information item, which can also be called from a database of the image recording apparatus and/or from an external database connected to the control computer 2, or a radiology information system. The contrast medium information item describes the availability of one or more contrast media for the future image recording as well as one or more properties of a respective available contrast medium. The contrast medium administration information item thus can designate a number of available contrast medium quantities for different available contrast media, each of which can be administered to the patient 4 for the future image recording to be performed. The contrast medium information item can further designate properties, dependent upon the image recording information item, of one or more of the available contrast media, so that these properties can be taken into account in the calculation of the contrast medium quantity. These properties can be, for example, a concentration of the contrast medium needed dependent upon the image recording to be carried out.

In addition to the contrast medium quantity, as part of the contrast medium administration information item, a point in time in the sequence of the image recording to be carried out in future is also determined. This determined point in time represents the most ideal point in time within the sequence of the image recording at which the contrast medium administration information item is displayed to the user of the image recording apparatus via the display 3. In the case of an image recording information item that includes a scan protocol or a sequence of multiple scan protocols to be carried out by the image recording scanner 1, point in time can be determined so that the display of the contrast medium administration information item takes place before a scan protocol, or a part of a scan protocol, which requires a contrast medium administration to the patient 4.

In step 7, the display of the contrast medium administration information on the display 3 of the image recording apparatus takes place. This occurs during the sequence of the image recording to be carried out by the image recording scanner 1 at the point in time determined as part of the contrast medium administration information item. The display of the contrast medium administration information item on the display 3 informs the user of the image recording apparatus of the contrast medium administration information item, and in particular to acknowledge the contrast medium quantity to be administered to the patient 4. In addition to the display of the contrast medium administration information item, a relevant part of the patient information item can be displayed on the display 3 simultaneously with the determined point in time. An example of such a display is described below with reference to FIG. 3. The relevant part of the patient information item can include a part of the patient information item that has an influence on the determination of the contrast medium administration information item and, in particular, an influence on the determination of the contrast medium quantity to be administered or, where relevant, the contrast medium to be administered. This can be, for example, the weight of the patient 4 and/or at least one laboratory value of the patient 4, such as a creatinine value as a measure for the renal function of the patient 4 and/or a contrast medium intolerance information item of the patient 4. The properties of the patient 4 that are relevant for the contrast medium administration are thus displayed to the user on the display 3 in parallel with the contrast medium administration information item at the determined point in time.

In step 8, following the display of the contrast medium administration information item and, if relevant, the part of the patient information item of relevance to the contrast medium administration, the method waits until an operation action of the user of the image recording apparatus takes place. This operation action can be that the user selects one of a number of contrast media described by the contrast medium administration information number. Furthermore, it is possible for the user to change the contrast medium quantity that was automatically determined as part of the contrast medium administration information. Once the user has made changes, or once the user has decided to make no changes, the user can generate a confirmation information item in step 9. This can be done, for example, via a user interface of the image recording apparatus, such as via a keyboard or a mouse of the control computer 2.

In step 10, the transfer of the contrast medium administration information item to an additional device 20 (see FIG. 1) of the image recording apparatus 1 takes place, which may be present in the recording apparatus in order to facilitate the contrast agent administration. The additional device 20 can communicate, for example via a wireless or a wired communication connection, with the control computer 2. The additional device 20 can be, for example, a device used for the image recording to be carried out by the image recording apparatus, such as a sensor or a local coil. The additional device 20 can be set or adapted dependent upon the contrast medium quantity stored in the contrast medium administration information. It is also possible for the additional device 20 to be a contrast medium pump, which is set or prepared by the transfer of the contrast medium administration information item in order to prepare a contrast medium administration corresponding to the contrast medium quantity stored in the contrast medium administration information item.

In step 11, the image recording takes place after the administration of the contrast medium to the patient 4. The contrast medium administration information item is stored together with image data recorded during the image recording as common storage data. The DICOM format, for example, can be used for the storage data, with the contrast medium administration information item being stored as metadata. In the event that a selection of a contrast medium and/or a further change to the contrast medium information item has been made by the user in step 8, this change is also stored as part of the storage data.

Figure 3:
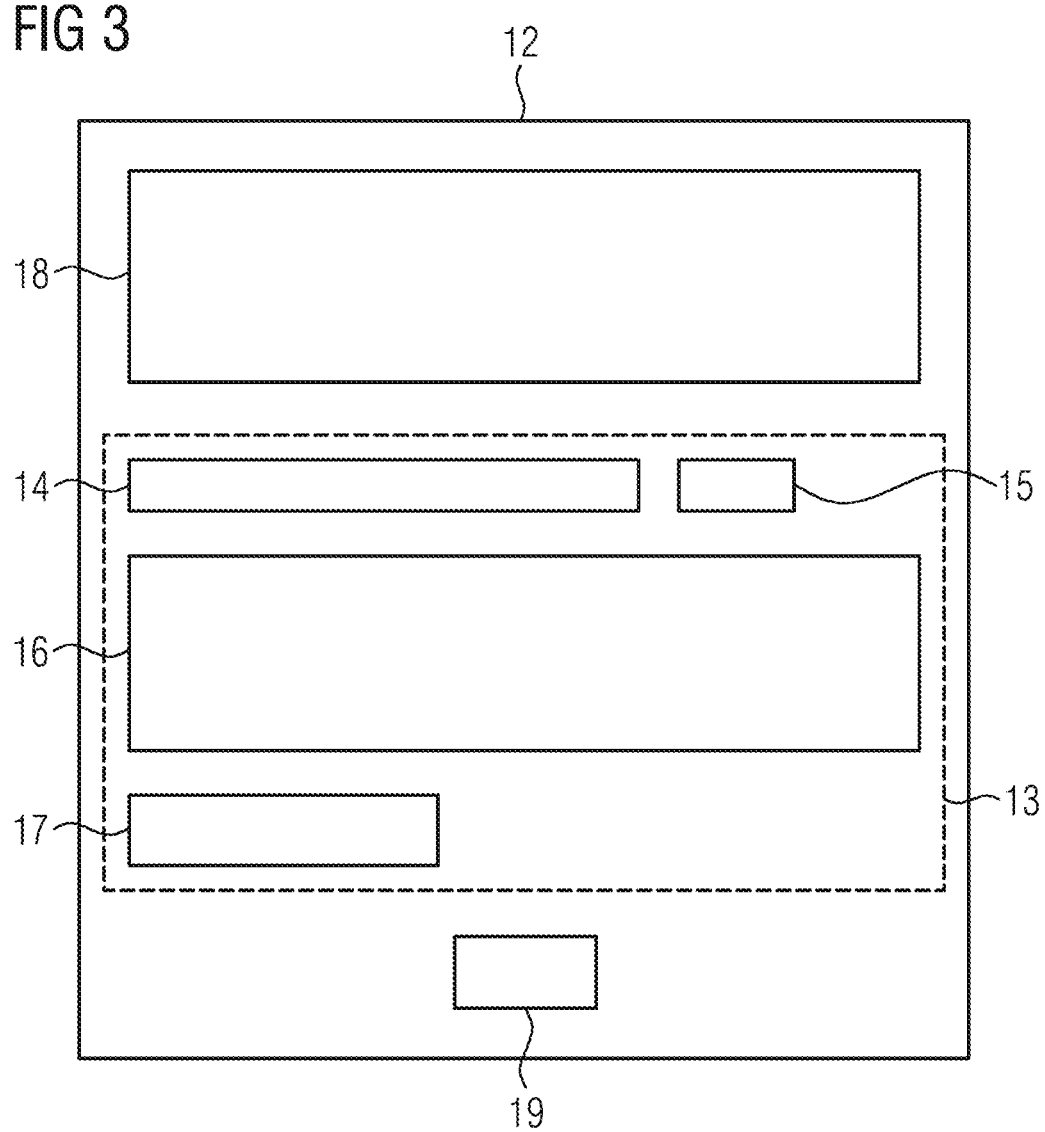
FIG. 3 schematically illustrates a display of a contrast medium administration information according to the invention.

FIG. 3 shows an exemplary embodiment of a common display of the contrast medium administration information item and of a relevant part of a patient information item. The window 12 shown in FIG. 3 can be displayed to the user of the image recording apparatus on a display 3 of the image recording apparatus configured as a screen. The contrast medium administration information item can be displayed, for example, within a region 13. For example, in a field 14, a designation or a type of the contrast medium to be administered can thereby be displayed. In the event that there is a number of contrast media available, a switching surface 15 can be displayed, by which the user can select one of the number of available contrast media. In addition, following the selection of the contrast medium displayed in the field 14, in the exemplary embodiment shown, one or more properties of the selected contrast medium are displayed in the field 16. This can involve, for example, a concentration in which a component of the contrast medium that is effective for the imaging is present in a dissolved form or as a suspension. Additionally, information regarding the component of the contrast medium effective for the imaging and a dosage of the contrast medium determined dependent upon the image recording information item can be specified.

The contrast medium quantity of the contrast medium specified in field 14 that is determined as part of the contrast medium administration information item and is to be administered to the patient for the future image recording is displayed in the region 17. This can be adapted by the user of the image recording apparatus as needed.

In the region 18, a display of the relevant part of the patient information item takes place. Thereby, in addition to the relevant part of the patient information, a further part of the patient information item, for example, the name of the patient can also be displayed. The relevant part of the patient information item can be, for example, the weight of the patient, the sex of the patient, the age of the patient, one or more laboratory values of the patient, for example, a creatinine value of the patient and/or information about a contrast medium intolerance of the patient. Advantageously, all the data relevant for the contrast medium administration to the patient 4 is therefore displayed to the user of the image recording apparatus at the determined point in time during the sequence of the future image recording. This enables a very efficient progress of the overall examination, since the different information items which can, if relevant, be stored on different databases and/or at different places within the radiology information system, do not have to be gathered together or determined by the user. The user can view all the relevant data advantageously at the most ideal possible point in time and, if relevant, amend it. Once the user has checked the information shown and/or, if relevant, undertaken a change of the contrast medium administration information item, he can create, for example, with a mouse click on an actuation field 19, a confirmation information item. Subsequently, transfer of the contrast medium administration information item to an additional device 20 takes place, and a contrast medium administration to the patient 4 is initiated. The sequence of the image recording to be carried out can be continued without notable pauses or interruptions for providing the contrast medium administration.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for operating an image recording apparatus comprising an image data acquisition scanner, said method comprising:
   with a control computer, operating the data acquisition scanner so as to execute an upcoming image data acquisition sequence during which at least one contrast medium is to be administered to a patient, the image data acquisition sequence comprising a magnetic resonance (MR) imaging sequence performed in accordance with an MR scan protocol;
   receiving, into said control computer, an image recording information item describing said image data acquisition, and receiving at least one patient information item describing a property of the patient,
   wherein the image recording information item comprises the MR scan protocol or a sequence of a plurality of MR scan protocols to be executed by said scanner in said image data acquisition, each MR scan protocol comprising control commands for operating said scanner in said image data acquisition;
   receiving, by said control computer, a contrast medium information item, the contrast medium information item describing availability of contrast media for said image data acquisition sequence and one or more properties of at least one contrast medium among the available contrast media, wherein the one or more properties of the at least one contrast medium are designated based on the image recording information item;
   in said control computer, determining a set of suitable contrast media from the available contrast media for the image data acquisition sequence based on the image recording information item;
   in said control computer, for each of the contrast media of the set of suitable contrast media, determining a respective contrast medium quantity based on the at least one patient information item;
   in said control computer, determining, based on the image recording information item, the at least one patient information item, and the contrast medium information item, a contrast medium administration information item comprising: a contrast medium to be administered to the patient from the set of suitable contrast media, the respective contrast medium quantity for the contrast medium to be administered to the patient, and a point in time in said image data acquisition sequence in which the contrast medium is to be administered; and
   from said control computer, displaying said administration information item at a display screen in communication with said control computer, at said point in time.

2. A method as claimed in claim 1 wherein the contrast medium information item is retrieved from a database accessible by said control computer.

3. A method as claimed in claim 1 comprising:
   after displaying said contrast medium administration information item at said display screen, receiving a user entry of a confirmation information item in said computer; and
   upon receiving said confirmation information item, transferring, from said control computer, said contrast medium administration information item to an additional device of said image recording apparatus in communication with said control computer, said additional device participating in said image data acquisition sequence.

4. A method as claimed in claim 3 comprising, after displaying said contrast medium administration information item, allowing the user to make a change entry into said control computer that changes said contrast medium administration information item to a changed contrast medium information item, and thereafter transferring said changed contrast medium information item from said control computer to said additional device.

5. A method as claimed in claim 1 comprising storing said contrast medium administration information item in a memory accessible by said control computer, together with image data acquired by execution of said image data acquisition, as common storage data.

6. A method as claimed in claim 5 comprising storing said common storage data in said memory in the DICOM format.

7. A method as claimed in claim 1 wherein receiving said image recording information item and said patient information item into said control computer comprises calling said image recording information item or said patient information item from a database accessible by said control computer.

8. A method as claimed in claim 7 wherein said database is a radiology information system.

9. A method as claimed in claim 1 wherein said patient information item contains information selected from the group consisting of a weight of the patient, at least one laboratory value of the patient, a creatinine value of the patient, and a contrast medium intolerance of the patient.

10. A method as claimed in claim 1 comprising displaying at least a part of the patient information item that is relevant for administration of the contrast medium, simultaneously at said display screen with the contrast medium administration information item at said point in time.

11. An image recording apparatus comprising:
    an image data acquisition scanner; and
    a control computer configured to:
      operate the data acquisition scanner so as to execute an upcoming image data acquisition sequence during which at least one contrast medium is to be administered to a patient, the image data acquisition sequence comprising a magnetic resonance (MR) imaging sequence performed in accordance with an MR scan protocol;
      receive (i) an image recording information item describing said image data acquisition, and (ii) at least one patient information item describing a property of the patient,
      wherein the image recording information item comprises the MR scan protocol or a sequence of a plurality of MR scan protocols to be executed by said scanner in said image data acquisition, each MR scan protocol comprising control commands for operating said scanner in said image data acquisition;
      receive a contrast medium information item, the contrast medium information item describing availability of contrast media for said image data acquisition sequence and one or more properties of at least one contrast medium among the available contrast media, wherein the one or more properties of the at least one contrast medium are designated based on the image recording information item;

determine a set of suitable contrast media from the available contrast media for the image data acquisition sequence based on the image recording information item;

for each of the contrast media of the set of suitable contrast media, determine a respective contrast medium quantity based on the at least one patient information item;

determine, based on the image recording information item, the at least one patient information item, and the contrast medium information item, a contrast medium administration information item comprising: a contrast medium to be administered to the patient from the set of suitable contrast media, the respective contrast medium quantity for the contrast medium to be administered to the patient, and a point in time in said data acquisition sequence in which the contrast medium is to be administered; and display said administration information item at a display screen in communication with said control computer, at said point in time.

12. A non-transitory, computer-readable data storage medium encoded with programming instructions, said storage medium being loaded into a control computer of an image recording apparatus comprising a data acquisition scanner, said programming instructions causing said control computer to:

operate the data acquisition scanner so as to execute an upcoming image data acquisition sequence during which at least one contrast medium is to be administered to a patient, the image data acquisition sequence comprising a magnetic resonance (MR) imaging sequence performed in accordance with an MR scan protocol;

receive (i) an image recording information item describing said image data acquisition, and (ii) at least one patient information item describing a property of the patient, wherein the image recording information item comprises the MR scan protocol or a sequence of a plurality of MR scan protocols to be executed by said scanner in said image data acquisition, each MR scan protocol comprising control commands for operating said scanner in said image data acquisition;

receive a contrast medium information item, the contrast medium information item describing availability of contrast media for said image data acquisition sequence and one or more properties of at least one contrast medium among the available contrast media, wherein the one or more properties of the at least one contrast medium are designated based on the image recording information item;

determine a set of suitable contrast media from the available contrast media for the image data acquisition sequence based on the image recording information item;

for each of the contrast media of the set of suitable contrast media, determine a respective contrast medium quantity based on the at least one patient information item;

determine, based on the image recording information item, at least one patient information item, and the contrast medium information item, a contrast medium administration information item comprising: a contrast medium to be administered to the patient from the set of suitable contrast media, the respective contrast medium quantity for the contrast medium to be administered to the patient, and a point in time in said data acquisition sequence in which the contrast medium is to be administered; and display said administration information item at a display screen in communication with said computer, at said point in time.

13. A method as claimed in claim 1 wherein, for each of the contrast media of the set of suitable contrast media, the respective contrast medium quantity is determined further based on one or more properties of the respective contrast media of the set of suitable contrast media.

14. A method as claimed in claim 1, wherein the point in time is selected by evaluating the control commands for operating the image data acquisition scanner with respect to a pre-scan initialization and/or calibration of the image recording apparatus.

15. A method as claimed in claim 1, wherein the contrast medium information item describing the availability of the contrast media for the image data acquisition sequence indicates which contrast media is present in a facility in which the image recording apparatus is operated.

16. A method as claimed in claim 1, wherein the point in time is from among a plurality of different points in time during the data acquisition sequence, each one of the respective plurality of different points in time being determined dependent upon properties of a respective available contrast medium.

17. A method as claimed in claim 1, wherein the point in time occurs in the data acquisition sequence occurs during part of an MR scan protocol in which the contrast medium is to be administered to the patient.

18. A method as claimed in claim 1, wherein the patient information item further comprises a measure of renal function of the patient.

* * * * *